United States Patent [19]
Petersen et al.

[11] Patent Number: 5,501,226
[45] Date of Patent: Mar. 26, 1996

[54] SHORT COHERENCE LENGTH, DOPPLER VELOCIMETRY SYSTEM

[75] Inventors: Christopher L. Petersen; Thomas Hellmuth, both of Danville, Calif.

[73] Assignee: Carl Zeiss, Inc., Thornwood, N.Y.

[21] Appl. No.: 325,675

[22] Filed: Oct. 19, 1994

[51] Int. Cl.$^6$ ...................................................... A61B 5/02
[52] U.S. Cl. ........................................... 128/691; 356/28.5
[58] Field of Search .................................... 128/691, 745, 128/664, 665, 666, 667, 661.08; 356/28, 28.5

[56] References Cited

U.S. PATENT DOCUMENTS

| | | | |
|---|---|---|---|
| 4,127,842 | 11/1978 | Hassler | 128/661.08 |
| 4,142,796 | 3/1979 | Riva | 356/28 |
| 4,166,695 | 9/1979 | Hill et al. | 128/691 |
| 4,346,991 | 8/1982 | Gardner | 356/28.5 |
| 4,402,601 | 9/1983 | Riva | 356/28.5 |
| 4,590,948 | 5/1986 | Nilsson | 128/666 |
| 4,637,716 | 1/1987 | Auweter et al. | 356/28.5 |
| 4,818,071 | 4/1989 | Dyott | 356/28.5 |
| 5,106,184 | 4/1992 | Milbocker | 351/221 |
| 5,240,006 | 8/1993 | Fujii et al. | 128/691 |
| 5,321,501 | 6/1994 | Swanson et al. | 356/345 |

FOREIGN PATENT DOCUMENTS

| | | | |
|---|---|---|---|
| 2531854 | 2/1984 | France | 128/666 |

OTHER PUBLICATIONS

Measurement of corneal thickness by low–coherence interferometry by C. K. Hitzenberger, *Applied Optics*, vol. 31, No. 31, 1 Nov. 1992, pp. 6637–6642.

Near–IR retinal laser Doppler velocimetry and flowmetry: new delivery and detection techniques, by B. L. Petrig and C. E. Riva, *Applied Optics*, vol. 30, No. 16, 1 Jun. 1991, pp. 2073–2078.

Scattering process in LDV from retinal vessels by C. E. Riva, B. L. Petrig, R. D. Shonat, and C. J. Pournaras, *Applied Optics*, vol. 28, No. 6, 15 Mar. 1989, pp. 1078–1083.

Retinal Circulation Time Determination using the SLO—Image Processing Techniques by P. G. Rehkopf et al., paper *First Int Symp Scan. laser Ophthal. and Tom.,* U. Eye Hospital, Munich, Germany, Jul. 7–8, 1989.

Optical Coherence Tomography by Huang et al., published in *Science*, 254, Nov. 22, 1991, pp. 1178–1181.

Bidirectional LDV system for absolute measurement of blood speed in retinal vessels by C. E. Riva et al., *Applied Optics*, vol. 18, No. 13, 1 Jul. 1979, pp. 2301–2306.

Huang, David et al, "Optical Coherence Tomography," Science vol. 254, Nov. 1991, pp. 1178–1181.

*Primary Examiner*—Angela D. Sykes
*Assistant Examiner*—Eric F. Winakur
*Attorney, Agent, or Firm*—Michael B. Einschlag

[57] ABSTRACT

Apparatus for measuring the speed of blood in blood vessels in biological samples, for example, in retinal blood vessels, which apparatus includes: (a) a source of a beam of radiation having a principal wavelength, which radiation is substantially spatially coherent and has a temporal coherence length which is less than 1 picosecond; (b) a beam splitter for splitting the beam into a sample beam and reference beam; (c) optical apparatus for directing the sample beam to an area within the biological sample; (d) a reflector for reflecting the reference beam; (e) a detector for detecting an interference between the sample beam reflected from the area and the reflected reference beam and for generating an interference signal; (f) apparatus for altering an optical path length of the reference beam from the beam splitter to the detector at an alteration velocity; and (g) an analyzer for analyzing the interference signal to determine the speed of the blood in the area from a shift of a central frequency of a frequency spectrum of the interference signal from a frequency determined from the alteration velocity and the principal wavelength.

19 Claims, 10 Drawing Sheets

SHORT COHERENCE LENGTH, DOPPLER VELOCIMETRY SYSTEM

TECHNICAL FIELD OF THE INVENTION

The present invention relates to a short coherence length Doppler velocimetry system.

BACKGROUND OF THE INVENTION

The human retina is sensitive to alterations in blood flow provided by the retinal vascular system. Such alterations in blood flow may: (a) occur as a result of a specific ocular disease such as blood vessel occlusion or (b) be associated with a systemic disease such as diabetes or systemic hypertension, which alterations in blood flow often lead to blindness. In light of this, an efficient, reproducible method for measuring blood flow in the retina is important for use in diagnosis and treatment of retinal vascular diseases.

A number of apparatus are known in the art for measuring/ estimating blood flow in the retina, however all suffer from one or more drawbacks. One such prior art apparatus is an ultrasound imaging system which measures a Doppler-shift in a reflected wave. The ultrasound imaging system uses a first technique to provide output to a user in a format known as Spectral Doppler flow mapping and a second technique to provide output to the user in a format known as Color Doppler flow mapping, which first and second techniques differ mainly in the manner in which data is presented to the user. The ultrasound imaging system suffers from a drawback in that neither the first nor the second technique can provide accurate three-dimensional localization of a signal, nor can these techniques account for the direction of blood flow relative to a direction of sound wave propagation (known in the art as "transducer alignment"). The inherent uncertainty in blood flow direction, referred to as transducer alignment error, can have large effects on the measured velocity. Furthermore, filter settings in the ultrasound apparatus can also have large effects on the absolute measured velocities. Filter induced errors, combined with transducer alignment errors, have the consequence that ultrasound Doppler techniques can provide only an averaged estimate of retinal blood flow.

Another such prior art apparatus is a Confocal Scanning Laser Ophthalmoscope ("CSLO") which can provide accurate three-dimensional images of the anterior eye, including the retina. Blood flow measurements in the retina have been made using the CSLO instrument by means of an indirect technique wherein fluorescent dyes are injected into the blood stream and video images of vascular structures under laser illumination are provided to show the spreading fluorescence. An indication of blood flow is provided by the strength of the time-dependent fluorescence. This technique suffers from a drawback in that it requires extensive post-processing of video images by a trained operator to extract gray scales and to correlate the gray scales with blood flow, see an article entitled "Retinal Circulation Time Determination using the SLO—Image Processing Techniques" by P. G. Rehkopf, J. W. Warnicki, L. J. Mandarino, T. R. Friberg, and D. N. Finegold, paper presented at the *First International Symposium on Scanning laser Ophthalmoscopy and Tomography*, University Eye Hospital, Munich, Germany, Jul. 7–8, 1989. A further drawback of this technique is that it requires injection of dyes into the blood stream.

Still another such prior art apparatus is a Laser Doppler Velocimeter ("LDV") which measures blood flow velocity in the retina by attaching a laser/detector system to a standard fundus camera, see an article entitled "Near-IR Retinal Laser Doppler Velocimetry and Flowmetry: New Delivery and Detection Techniques" by B. L. Petrig and C. E. Riva, *Applied Optics* 30, 1 Jun. 1991, pp. 2073–2078. The LDV technique can provide localized (on a 2-D plane), absolute measurement of blood flow velocity in major retinal vessels (>50 μm diameter) in a non-invasive manner. However, the standard LDV technique suffers from several drawbacks. First, the LDV technique suffers a drawback in that it cannot provide 3-D localization by itself. Second, the LDV technique suffers a drawback in that it includes simultaneous measurement of all blood velocities within a blood vessel (as is well known, blood flows fastest in the center of the blood vessel and slowest at the wall). The presence of all blood velocities within a detection signal: (a) complicates the analysis and, (b) when short sampling times are used to avoid multiple scattering artifacts, makes interpretation of the detection signal difficult. This is illustrated in FIG. 1A where, for the LDV technique, the coherence length 210 of laser beam 220 is much greater than the diameter of blood vessel 200. Third, the LDV technique suffers a drawback in that it includes multiple scattering artifacts. Multiple scattering effects are disadvantageous because multiple scattering tends to dominate the reflected signal over long sampling times, thereby making velocity determination difficult. As a result, one is forced to use short sampling times. This is illustrated in FIGS. 1B and 1C. FIG. 1B shows, in graphical form, a frequency spectrum of a measured LDV signal for an idealized blood sample, i.e., a very dilute blood sample in which only single scattering need be considered. For this idealized case of single scattering, the measured LDV signal frequency spectrum is constant with respect to frequency up to a maximum frequency, $f_{max}$, where it abruptly drops to the shot noise limit. This behavior is caused by the parabolic red blood cell velocity profile found in blood vessels. The parabolic velocity profile causes each velocity increment (corresponding to a Doppler frequency increment) to contribute an equal amount to the measured LDV signal strength and this produces a flat frequency spectrum. Beyond $f_{max}$ there is no further signal, except for the noise terms. In contrast to the idealized case of single scattering shown in FIG. 1B, FIG. 1C shows a representative spectrum from actual blood vessels wherein multiple scattering forces the use of very short sample times. The use of short sample times, in turn, makes exact determination of $f_{max}$ difficult because the reflected signal is naturally stochastic and, as a result, short sampling times increase the noise. However, long sample times allow the signal beyond $f_{max}$ to build up (multiple scattering can cause frequency shifts larger than $f_{max}$). Therefore, determining the cut-off frequency $f_{max}$ is possible only for short sampling times. Fourth, the LDV technique suffers a drawback in that it relies on reflection from the blood vessel wall as a "local oscillator" (the blood vessel wall provides a strong, non-Doppler-shifted reference beam). Interference between the local oscillator beam and the Doppler-shifted signal causes a low-frequency beat signal in the detector from which the velocity can be extracted. However, the beat frequencies are typically a few kilohertz and are therefore sensitive to low frequency 1/f noise which is inherent in the LDV apparatus.

In light of the above, there is a need in the art for an apparatus for providing non-invasive, blood flow velocity measurement which overcomes the above-described problems.

SUMMARY OF THE INVENTION

An embodiment of the present invention is an apparatus for providing noninvasive, blood flow velocity measurements which overcomes the above-described problems in the art. In particular, an embodiment of the present invention comprises a Michelson interferometer which includes a short coherence length light source.

Embodiments of the present invention provide the following advantages: (a) excellent three-dimensional (3-D) spatial localization of the signal; (b) independence from non-Doppler-shifted light reflected from blood vessel walls; (c) multiple scattering effects are minimized; and (d) the reference beam can be modulated at frequencies well above the 1/f noise of the instrument. These advantages occur for the following reasons. A first reason for the advantages of the present invention is that the short coherence length requires the reference and sample arms of the interferometer be balanced, i.e., to have the same optical length, to within the coherence length of the light source (for example, the use of a superluminescent light emitting diode source can provide temporal coherence lengths on the order of 30–60 femtoseconds and, as a result, can provide optical lengths on the order of 10–20 μm). This balance, in turn, requires accurate location of a reference mirror and, therefore, provides an accurate measurement of position of a reflected sample beam (for example, the z coordinate or depth of the point of reflection). In addition, a fundus camera and/or standard scanning optics used to steer the sample beam provides an accurate measurement of the (x,y) coordinates of the point of reflection of the sample beam. A second reason for the advantages of the present invention is that the 3-D spatial localization allows Doppler-shifted light arising from the center of a blood vessel to be independent of non-Doppler-shifted light arising from a wall of the blood vessel. As a result, signal analysis is simplified and less ambiguous. A third reason for the advantages of the present invention is that multiple scattering effects are minimized since, in blood vessels, multiple scattering of light occurs over distances large compared to the coherence length of the short coherence length source. A fourth reason for the advantages of the present invention is that the reference beam can be modulated at frequencies well above the 1/f noise of the instrument, improving the signal-to-noise ratio of the measured Doppler shifts. Thus, in accordance with a preferred embodiment of the present invention which overcomes the 1/f noise problem, a separate reference beam is utilized that allows the signal to be frequency-shifted well above the 1/f noise.

In particular, a first embodiment of the present invention is apparatus for measuring the speed of red blood cells (RBC) in blood vessels in biological samples, for example, in retinal blood vessels, which comprises: (a) a source of a substantially spatially coherent beam of radiation that also displays a short temporal coherence (preferably a temporal coherence which is less than 1 picosecond); (b) means for splitting the beam into a sample and reference beam; (c) means for directing the sample beam to an area within the biological sample (d) translatable reflecting means disposed in a path of the reference beam; (e) detector means for detecting an interference between the sample beam reflected from the biological sample and the reference beam reflected from the translatable reflecting means; (f) optional modulator means disposed in the reference beam path to modulate the reference beam at high frequency when needed; and (g) analyzer means for measuring the temporal and frequency component of the detected interfering light and for determining the RBC speed based on these measurements.

In a preferred embodiment of the present invention: (a) the light source is a superluminescent light emitting diode which is focused: (i) through a pinhole aperture or (ii) into a single mode optical fiber to provide good spatial coherence; (b) the sample and reference beams are produced by a beam splitter; (c) means for directing the sample beam to a specific area within the biological sample comprises a fundus camera or a slit lamp biomicroscope with fundus viewing optics; (d) the detector means comprises a photodiode or similar device; (e) the translatable reflecting means comprises a retroreflector mounted on a galvanometer or similar apparatus; and (f) the analyzer means comprises a gated timer and a frequency to voltage converter or a microprocessor controller or equivalent.

In a second embodiment of the present invention, the accuracy of the apparatus is improved by directly monitoring the actual speed of the retroreflector in the path of the reference beam ("reference mirror"). All galvanometers exhibit, to varying degrees, small velocity changes as they scan along their range of motion. These velocity changes show up as a frequency band about a central beat frequency in the interference signal output by the detector. Since the measured blood velocity is only accurate to within the velocity uncertainty of the reference mirror, the uncertainty can be reduced, or removed, by accurately measuring the velocity of the reference mirror at all points during its travel. Many galvanometers are equipped with a mechanism that provides a direct electrical indication of relative position. In this second embodiment, the electrical signal provided by the galvanometer is electronically differentiated, the differential being proportional to the velocity, and the velocity information is supplied to the analyzer for use in correcting the measured blood speeds.

In a third embodiment of the present invention, the galvanometer speed is also monitored, but by interferometric means which provide greater accuracy and reliability than differentiating the electrical signal as described above. However, the interferometric method is more costly. In this third embodiment, a long coherence length source (for example, a distributed feedback diode laser common in the telecommunications industry) is used in a Michelson interferometer set-up, where now the galvanometer-mounted reference mirror becomes the sample mirror, and a simple fixed mirror is used for the reference arm. Since the coherence length is now long, the two arms do not have to be balanced in length. The resulting interference signal will have a beat frequency which is directly proportional to the galvanometer speed. This frequency information can be used by the analyzer unit to correct the measured blood speed.

BRIEF DESCRIPTION OF THE FIGURE

Components which are the same in the various figures have been designated by the same numerals for ease of understanding.

DETAILED DESCRIPTION

We have discovered that the shortcomings of prior art retinal LDV systems stem from the fact that long-coherence length sources, i.e., lasers, were used. These shortcomings are overcome by embodiments of the present invention which comprise a Michelson interferometer which includes a short coherence length light source.

Figure 2A:
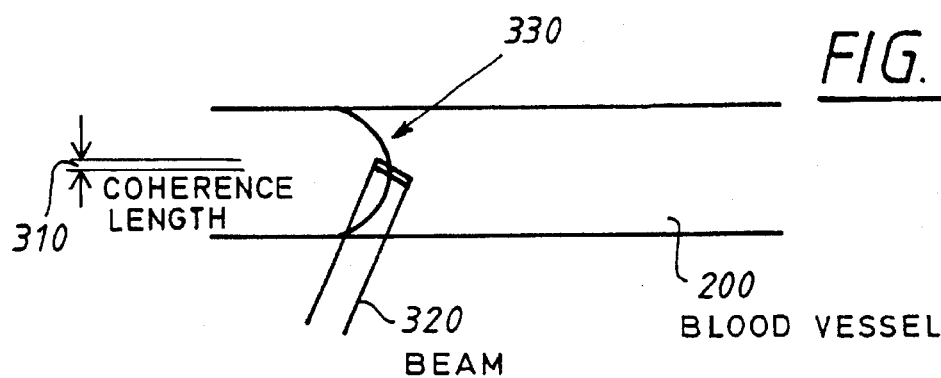
FIGS. 2A, 2B, and 2C provide an aid in understanding the advantages of the inventive short coherence length Doppler velocimetry system.
Figure 2B:
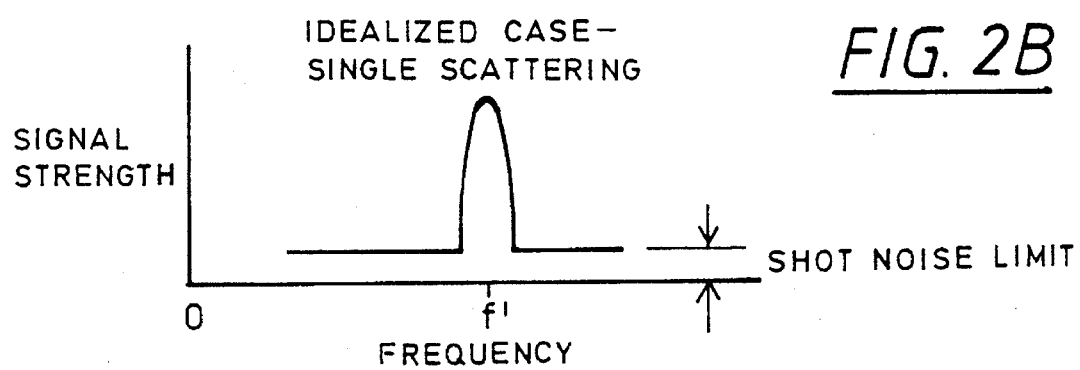
Figure 2C:
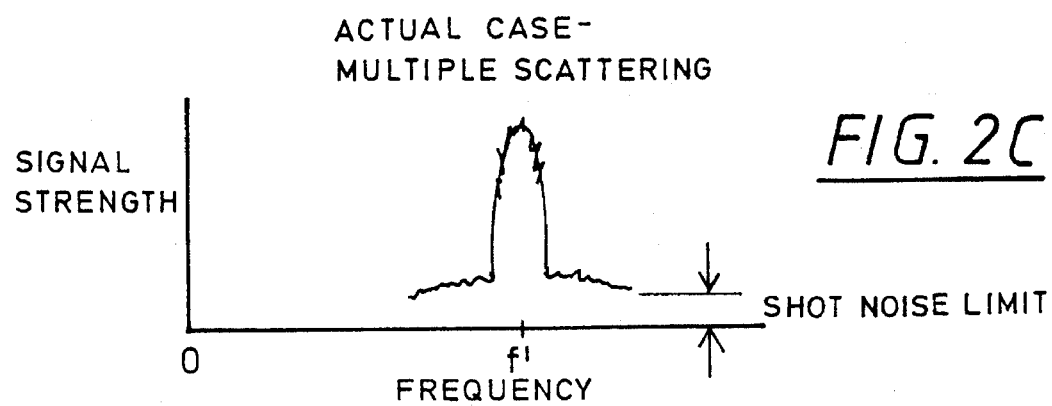

Embodiments of the present invention provide the following advantages: (a) excellent three-dimensional (3-D) spatial localization of the signal; (b) independence from non-Doppler-shifted light reflected from blood vessel walls; (c) multiple scattering effects are minimized; and (d) the reference beam can be modulated at frequencies well above the 1/f noise of the instrument. These advantages occur for the following reasons. A first reason for the advantages of the present invention is that the short coherence length requires the reference and sample arms of the interferometer to be balanced, i.e., to have the same optical length, to within the coherence length of the light source (for example, the use of a superluminescent light emitting diode source can provide temporal coherence lengths on the order of 30–60 femtoseconds and, as a result, can provide optical lengths on the order of 10–20 μm). This balance, in turn, requires accurate location of a reference mirror and, therefore, provides an accurate measurement of position of a reflected sample beam (for example, the z coordinate or depth of the point of reflection). In addition, a fundus camera and/or standard scanning optics used to steer the sample beam provides an accurate measurement of the (x,y) coordinates of the point of reflection of the sample beam. A second reason for the advantages of the present invention is that the 3-D spatial localization allows Doppler-shifted light arising from the center of a blood vessel to be independent of non-Doppler-shifted light arising from a wall of the blood vessel. As a result, signal analysis is simplified and less ambiguous. This is illustrated in FIG. 2A where the coherence length 310 of short coherence beam 320 is much shorter than the diameter of blood vessel 200. Further, the measured signal can be obtained so that it arises only from a small section near the center of the vessel and, thereby, the maximum of blood velocity profile 330 (the spot size can approach 20 μm in diameter and the coherence length is ~10 μm). A third reason for the advantages of the present invention is that multiple scattering effects are minimized since, in blood vessels, multiple scattering of occurs over distances which are large compared to the coherence length of the short coherence length source. This is illustrated in FIGS. 2B and 2C. FIG. 2B shows, in graphical form, a frequency spectrum of a measured signal for an idealized blood sample, i.e., a very dilute blood sample in which only single scattering need be considered. For an idealized case of single scattering, the measured signal frequency spectrum is essentially very weak with respect to frequency, except for a frequency corresponding to the Doppler shift provided by the moving blood. As one can readily appreciate, this behavior provides for straightforward analysis of blood velocity. The behavior of the idealized case of single scattering shown in FIG. 2B is maintained for the representative spectrum obtained from actual blood vessels shown in FIG. 2C, which spectrum includes the effects of multiple scattering. A fourth reason for the advantages of the present invention is that the reference beam can be modulated at frequencies well above the 1/f noise of the instrument, thereby improving the signal-to-noise ratio of the measured Doppler shifts. Thus, in accordance with a preferred embodiment of the present invention which overcomes the 1/f noise problem, a separate reference beam is utilized that allows the signal to be frequency-shifted well above the 1/f noise.

Figure 3:
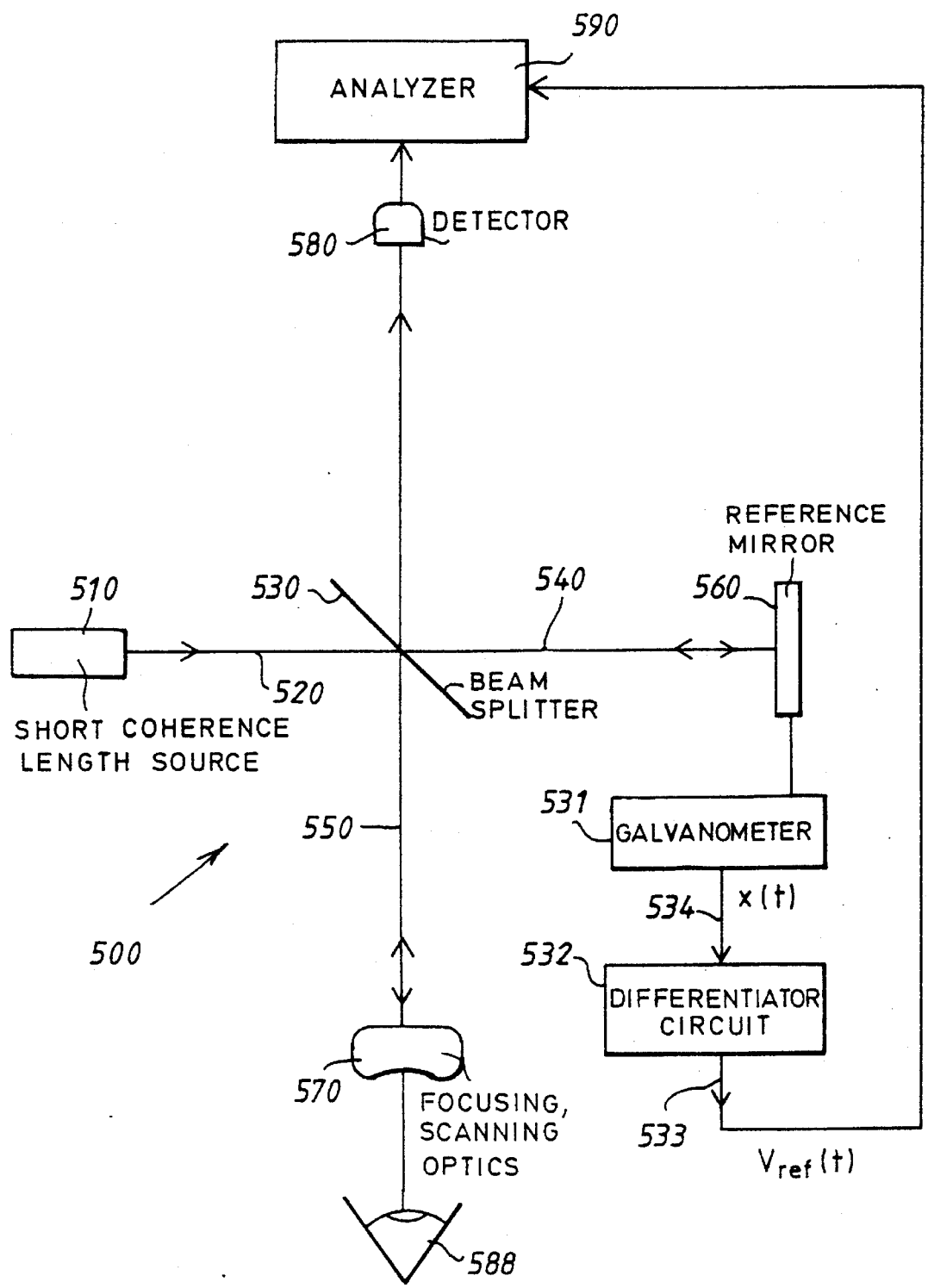
FIG. 3 shows, in pictorial form, an embodiment of the present invention which compensates for uncertainties in galvanometer speed.

FIG. 3 shows, in pictorial form, embodiment 500 of the present invention. As shown in FIG. 3, short coherence length source 510 emits beam 520 and beam 520 is split at beam splitter 530 (preferably) into two, substantially equal intensity beams, reference beam 540 and sample beam 550. As shown in FIG. 3, reference beam 540 is directed towards reference mirror 560 and sample beam 550 is directed towards focusing and scanning optics 570. Reference mirror 560 is translated at a substantially constant velocity by galvanometer 531. Focusing and scanning optics 570 is means for directing sample beam 550 to a specific area within eye 588. For example, the focusing and scanning optics may be a fundus camera or a slit lamp biomicroscope with fundus viewing optics or scanning optics including orthogonally mounted scanning mirrors, all of which are well known to those of ordinary skill in the art. An embodiment of focusing and scanning optics will be described in detail below in conjunction with FIG. 6. Reference beam 540 is reflected from reference mirror 560 so that it travels back to beam splitter 530 and sample beam 550 is reflected back from eye 588 so that it travels back through focusing and scanning optics 570 to beam splitter 530. At beam splitter 530 the two reflected beams converge and interfere. Beam splitter 530 causes the reflected beams to be directed partially towards detector 580 and partially towards source 510. The relative amounts of each portion depends on the nature of the interference at that moment, i.e., constructive/destructive interference. The output from detector 580 is applied as input to analyzer 590 which analyzes the signal in accordance with the teaching of Appendix A. An embodiment of analyzer 590 will be described in detail below in conjunction with FIGS. 8A–8D and 9.

As illustrated in FIG. 3, in accordance with the present invention, reference mirror 560 is scanned at substantially constant velocity, $v_r$, in a predetermined direction (either towards or away from beam splitter 540). The scan length is variable, but is held constant for a given measurement, typical lengths are on the order of a few millimeters. After a scan, reference mirror 560 is returned to its starting position and another scan is taken. Although data may be obtained from the return motion of reference mirror 560, this is not always done for simplicity. Note that the scan of reference mirror 560 provides the scan of eye 588 in the z-direction or in depth.

Figure 8A:
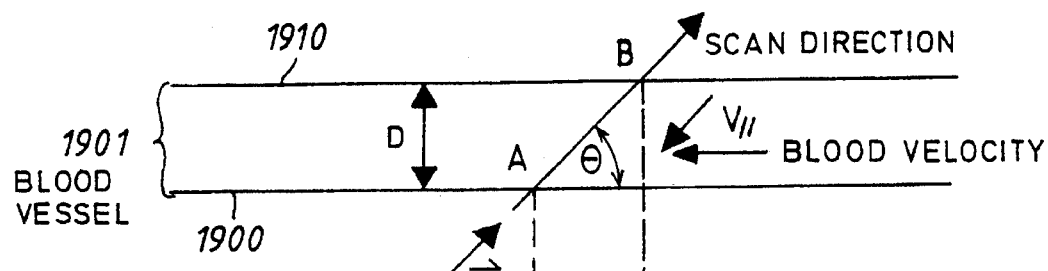
FIGS. 8A, 8B, and 8C illustrate, in pictorial form, signals obtained from the detector of the embodiment of FIG. 3.
Figure 8B:
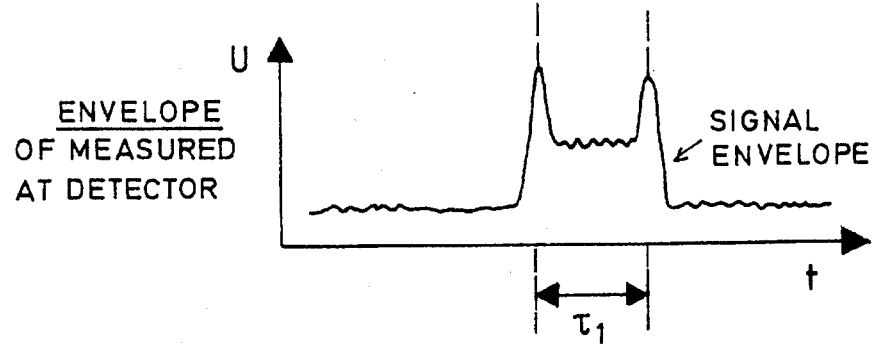

The following discussion is made in conjunction with FIGS. 8A–8D which illustrate, in pictorial form, signals obtained from detector 580 of embodiment 500 of FIG. 3. Whenever reference mirror 560 is at a position such that the reference arm optical path length matches the sample arm optical path length corresponding to near wall 1900 of blood vessel 1901 (this is indicated by point A shown in FIG. 8A), a relatively large non-Doppler shifted interference signal will be observed at detector 580. As the scan of reference mirror 560 progresses, interference signals will be recorded that correspond to Doppler-shifted light which is reflected from moving red blood cells inside blood vessel 1901. At far wall 1910 of blood vessel 1901 (this is indicated by point B shown in FIG. 8A), another relatively large non-Doppler shifted interference signal will again be observed at detector 580. The envelope of the signal output from detector 580 is shown in FIG. 8B. Time $\tau_i$ shown in FIG. 8B is given by the diameter of blood vessel 1901 D divided by the product of sin θ and $v_r$, where θ is defined in FIG. 8A, i.e., $\tau_i = D/(\sin\theta * v_r)$. Typical values for D, θ, and $v_r$ are: D=100 microns, θ=60°, and $v_r$=16 cm/sec, which typical values give $\tau_i$ equal to about 720 microseconds. The signal shown in FIG. 8B consists of rapidly varying beats and the frequency of the beats depends on both the Doppler shifts from moving reference mirror 560 and from the moving red blood cells.

In accordance with eqn. (A7) of Appendix A, the peak of the frequency spectrum obtained by Fourier transforming a time segment of the signal output by detector 580 occurs at a center frequency f' where: (a) f'=2v'/λ; (b) λ, is the central wavelength of short coherence length source 510; (c) v'=$v_r \pm v_\parallel$; (d) $v_\parallel$ is the component of red blood cell (RBC) velocity which is parallel or anti-parallel to the direction of sample beam 550 (see FIG. 8A); and (e) $v_r$ is the velocity of reference mirror 560. In a preferred embodiment of the present invention, $v_r$ is approximately 16 cm/sec and, for λ=818 nm; this gives $f_r$ being about 400 kHz, i.e., a frequency which is well above the 1/f noise of the interferometer. Therefore, within time window $\tau_i$, the frequency shift relative to the Doppler frequency of reference mirror 560 starts at zero at near wall 1900 of blood vessel 1901, reaches a maximum at the center of blood vessel 1901 where the red blood cell velocity is greatest, and decreases again to zero at far wall 1910 of blood vessel 1901. The high frequency components of the signal output from detector 580 are shown in FIG. 8C.

To extract the red blood cell velocity information from the signal output from detector 580, small time segments of the signal have to be analyzed separately. The optimal length of the time segments is $\tau_s$, where $\tau_s$ is given by the coherence length $l_c$ of light source 510 divided by $v_r$. Typical values are $l_c$=14 microns and $v_r$=16 cm/sec which result in $\tau_s$ being approximately equal to 88 microseconds. FIG. 8D shows two such time segments, one at near wall 1900 of blood vessel 1901 and one at the center of blood vessel 1901 (the time segment at the center of blood vessel 1901 is delayed by $\tau_d$ seconds, where $\tau_d$ is one-half of $\tau_i$). FIG. 8D shows the two time segments of the signal shown in FIG. 8C where the dots on the signals represent sample points taken by analyzer 590.

Figure 9:
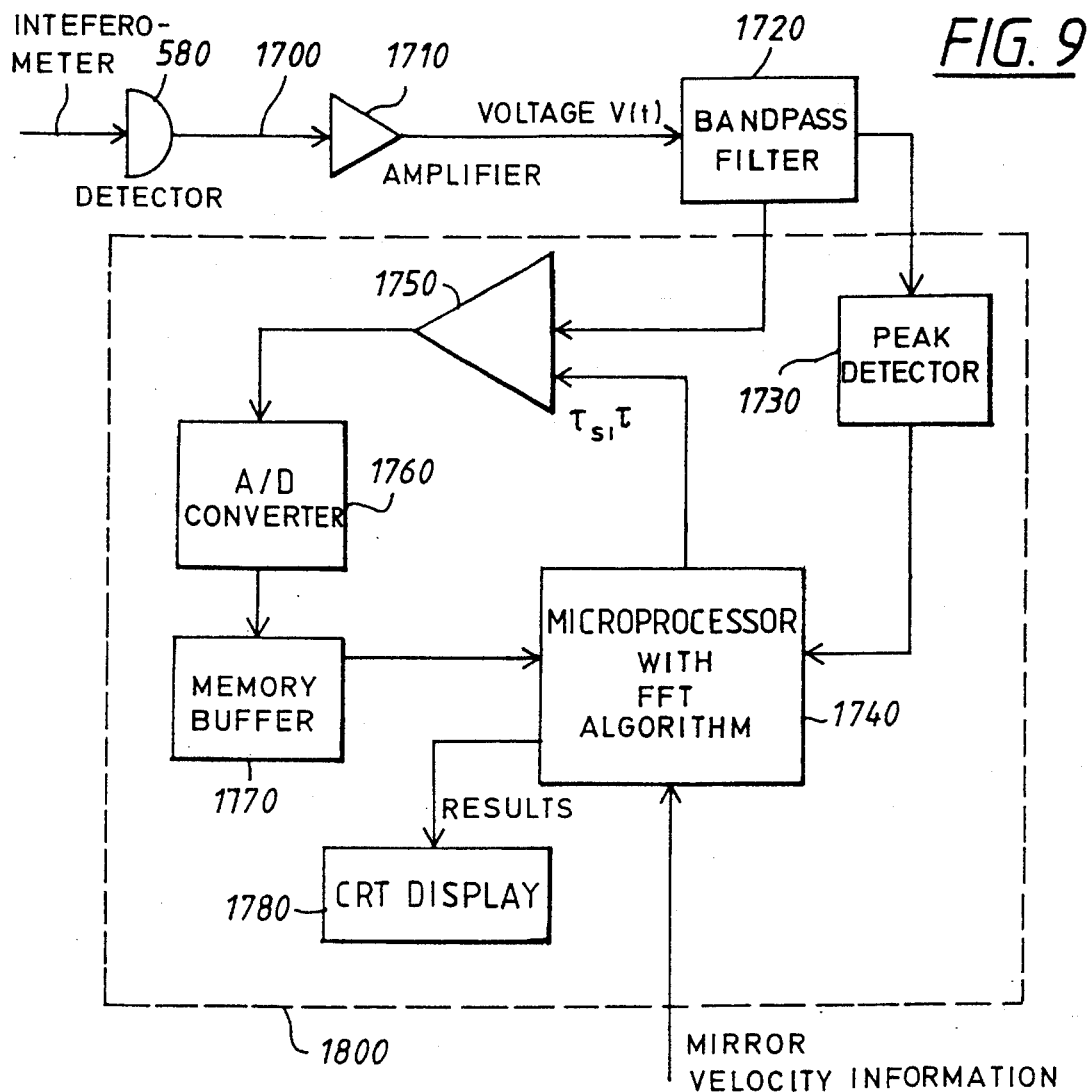
FIG. 9 shows a block diagram of one embodiment of the analyzer of FIG. 3.

FIG. 9 shows a block diagram of an embodiment of analyzer 590 which is fabricated in accordance with the present invention. As shown in FIG. 9, signal 1700 output from detector 580 is applied as input to amplifier 1710. The amplified output from amplifier 1710 is applied as input to bandpass filter 1720. Bandpass filter 1720 is centered at frequency $f_r$=2$v_r$/λ. The width of bandpass filter 1720 is chosen to limit extraneous noise components while ensuring that the additional frequency shifts about $f_r$ caused by the red blood cells are not rejected. As those skilled in the art will readily appreciate, the center frequency f' of the frequency spectrum of the signal segments will be above or below $f_r$, the frequency of moving reference mirror 560, depending on whether $v_\parallel$ is parallel or antiparallel to the direction of the sample beam. In practice, for the case of moving reference mirror 560 shown in FIG. 3, $f_r$ is approximately equal to 400 kHz and the bandpass width is ±40 kHz.

Figure 8C:
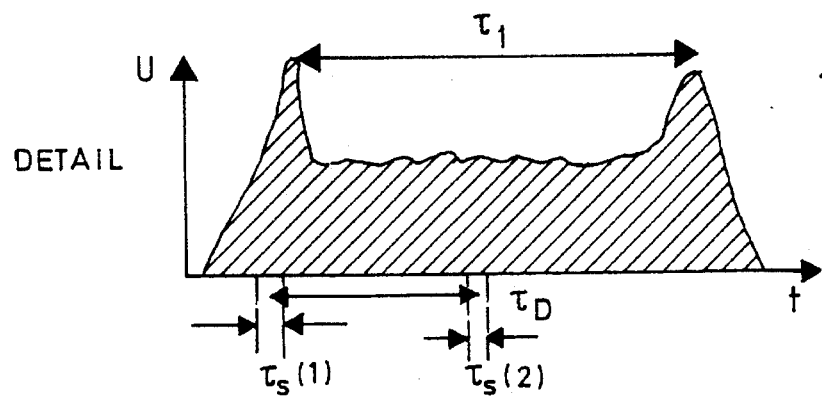
Figure 8D:
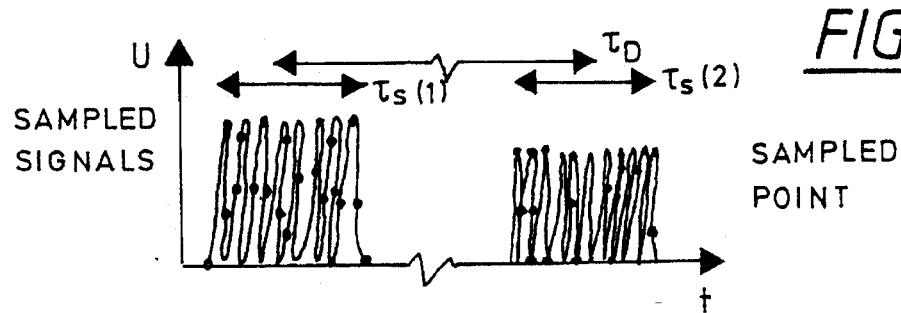

The output from bandpass filter 1720 is applied as input to peak detector 1730 to detect the signal peaks shown in FIGS. 8B and 8C. The output from peak detector 1730 is applied as input to microprocessor 1740. The detection of the first of the peaks shown in FIGS. 8B and 8C indicates the detection of near wall 1900. Further, the time of detection of the first and second peaks can be used to determine $\tau_i$ and $\tau_d$, i.e., $\tau_d$ is one-half of $\tau_i$. In order to measure the segments of the signal output from detector 580, microprocessor 1740 transmits a signal to timed gate 1750 which causes timed gate 1750 to be open for $\tau_s$ seconds. Further, microprocessor 1740 delays the opening of timed gate 1750 for an amount of time equal to τ seconds after detection of the first peak. The output from timed gate 1750 is applied as input to analog-to-digital converter 1760 (A/D 1760) where the signal is sampled and converted to digital format. The digital output from A/D 1760 is stored in memory buffer 1770. Microprocessor 1740 analyzes the digital data stored in memory buffer 1770 using a standard FFT algorithm and determines $v_\parallel$. As one can readily appreciate, for the embodiment shown in FIG. 9, the various time segments of the signal output from detector 580 are analyzed on succeeding scans of moving reference mirror 560 where microprocessor 1740 increases τ so that timed gate 1750 samples time segments across the entire signal to obtain data including the entire blood vessel. As those of ordinary skill in the art can readily appreciate, alternative embodiments include use of a multiplicity of gates to simultaneously sample different time segments of the signal from a single scan or include converting the entire signal to digital form and storing the entire signal in digital form for subsequent analysis of the various time segments from the same scan. In addition, the results obtained for each of the time segments may be averaged over many scans, depending on the accuracy desired and the noise of the detector output signal.

Microprocessor 1740 displays the results of the analysis, for example, a graph of $v_\parallel$ across the blood vessel, on CRT 1780. Note that further results are described below. Further note that FIG. 9 shows mirror velocity information being input to microprocessor 1740, which mirror velocity information is utilized in performing the analysis in the manner which was described above and in Appendix A. However, a detailed description of how mirror velocity information is obtained where the velocity varies is provided below in conjunction with FIGS. 3 and 4. It should be understood that the components shown in FIG. 9 represent just one of many possible implementations of analyzer 590. For example, it is understood that all of the elements in FIG. 9 which are enclosed within dotted line 1800 in FIG. 9 could be accomplished by a microprocessor.

In accordance with the present invention, source 510 is a substantially spatially coherent beam of radiation that also displays a short temporal coherence, preferably a temporal coherence which is much less than a picosecond, for example, on the order of 30–60 femtoseconds. It is preferred to have a substantially spatially coherent beam of radiation to ensure that the waves impinging upon the sample region in the eye are essentially plane waves to help prevent other interferences which would mask the interferometer effects desired to be measured. In addition, good spatial coherence enables the radiation to be more efficiently coupled into fibers for embodiments described below which utilize single mode fibers. Beams with poor spatial coherence have high beam divergence, such beam divergence being beyond the acceptance angle of single mode fibers. In a preferred embodiment of the present invention: (a) source 510 comprises a superluminescent light emitting diode (for example, emitting at about 818 nm) which is focused: (i) through a pinhole aperture or (ii) into a single mode optical fiber to provide good spatial coherence; (b) detector 580 comprises a photodiode or similar device; (c) reference mirror 560 comprises a retroreflector; and (d) analyzer 590 comprises a gated timer and a frequency to voltage converter or a microprocessor controller or equivalent apparatus. Note that when reference mirror 560 is a retroreflector, equations defining $f_r$ by $f_r=2v_r/\lambda$ should now define $f_r$ by $f_r=4v_r/\lambda$ and all frequencies discussed above with respect to the described embodiments need to be recalculated accordingly.

Galvanometers, like galvanometer 531 shown in FIG. 3 which is used to translate reference mirror 560, exhibit, to varying degrees, small velocity changes as they scan along their range of motion. These velocity changes show up as a frequency band about the central beat frequency in the interference signal output by detector 580. Further, since the measurement of blood velocity is accurate to within the velocity uncertainty of reference mirror 560, the uncertainty can be reduced, or removed, by accurately measuring the velocity of reference mirror at all points during its travel. Many galvanometers are equipped with a mechanism that provides a direct electrical indication of relative position. In accordance with the present invention, electrical position signal 534 output from galvanometer 531 is applied as input to differentiator circuit 532. Differentiator circuit 532 differentiates electrical position signal 534 to produce velocity signal 533 which is proportional to velocity. Velocity signal 533 ($V_{ref}(t)$ of FIG. 3) is applied as input to analyzer 590 where it is used to determine $f_r$ from $f_r=2V_{ref}(t)/\lambda_o$ (where $\lambda_o$ is the peak wavelength of the light source). Since the velocity of mirror 560 is much greater than the red blood cell velocity, the Doppler shift caused by the red blood cells ($f_{RBC}=2V_{RBC}(t)/\lambda_o$) will show up as a frequency shift from $f_r$, i.e., the measured Doppler frequency is $f_r \pm f_{RBC}$ where the $\pm$ arises because the red blood cells move both toward and away from the detector. As those of ordinary skill in the art can readily appreciate, the differentiation of galvanometer position signal 534 can occur either through an electronic circuit like differentiator circuit 532 or it can be computed by analyzer 590. As shown in FIG. 9, $V_{ref}(t)$ is input to microprocessor 1740. In analyzing data from a time segment of the signal output from detector 580, microprocessor 1740 now utilizes the value of $V_{ref}(t)$ which corresponds to that time segment. As those of ordinary skill in the art should readily appreciate, $V_{ref}(t)$ may be averaged over a time segment if differentiator circuit 532 provides sufficient data. Again, note should be taken of the proper equation to use for $f_r$ when a reference mirror 560 is a retroreflector.

Figure 4:
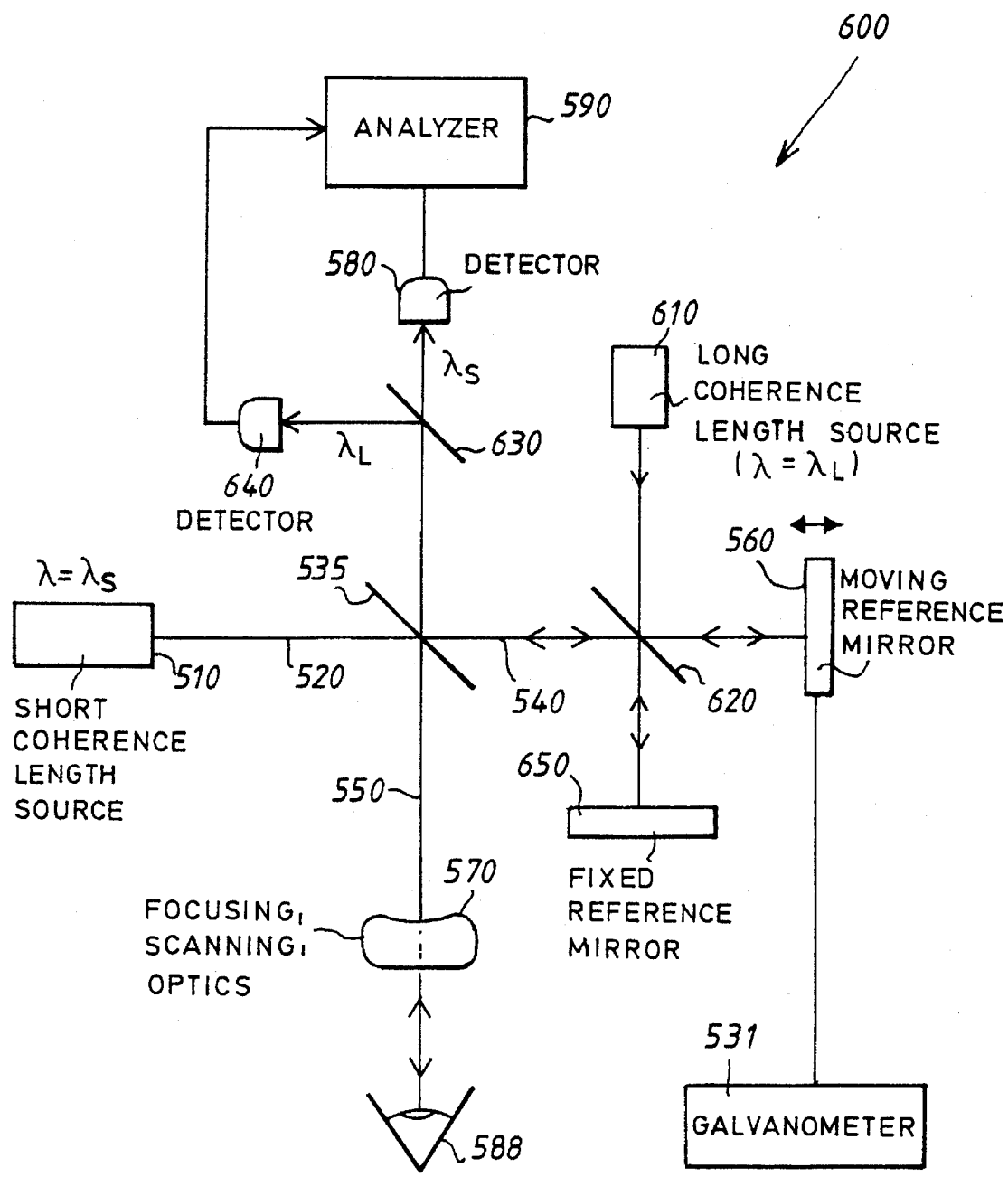
FIG. 4 shows, in pictorial form, a further embodiment of the present invention which corrects for uncertainties in galvanometer speed.

FIG. 4 shows, in pictorial form, a further embodiment 600 of the present invention which corrects for galvanometer velocity uncertainty using interferometric means which provide greater accuracy and reliability than is obtained by differentiating an electrical signal in accordance with the embodiment shown in FIG. 3. Components which are the same in FIGS. 3 and 4 have been designated by the same numerals for ease of understanding. As shown in FIG. 4, a second interferometer is created using long coherence length source 610 having output with a wavelength ($\lambda_L$) that is different from the wavelength ($\lambda_s$) of short coherence length source 510. In accordance with the present invention, long coherence length of source 610 must be longer than the length of travel of reference mirror 560 (typically ~3 mm). Beam splitters 530, 620, and 630 are 50% reflective at wavelength $\lambda_L$ and are substantially fully transmissive at wavelength $\lambda_s$. Detector 580 is substantially sensitive only to $\lambda_s$ while detector 640 is substantially sensitive only to $\lambda_L$. As one can readily appreciate from this, in the second interferometer, galvanometer-mounted reference mirror 560 becomes the sample mirror and fixed mirror 650 is the reference mirror. Since the coherence length of source 610 is long, the two arms of the second interferometer do not have to be balanced in length. Then, in accordance with the present invention, detector 640 outputs a signal whose frequency is directly proportional to the speed of reference mirror 560, i.e., the resulting interference signal will have a beat frequency $f_B$ which is directly proportional to the speed of reference mirror 560 $v_r$ ($f_B=2v_r/\lambda_L$.) The output from detector 640 is applied as input to analyzer 590 and analyzer 590 uses the frequency information to measure the velocity of reference mirror 560 and, in turn, to measure the red blood cell velocity. In particular, for an embodiment of analyzer 590 like that shown in FIG. 9, the signal from detector 640 would be bandpass filtered, gated, converted to digital, and Fourier transformed to detect $f_B$ as the peak of the frequency spectrum for the relevant time segments used in analyzing the output from detector 580. In a preferred embodiment of the present invention, long coherence source 610 is a distributed feedback diode laser running at 1350 or 1550 nm (which lasers are fabricated for use in the telecommunications industry), short coherence source 510 is a superluminescent light emitting diode running at 820 nm, detector 580 is a silicon photodiode and detector 640 is an indium gallium arsenide (InGaAs) photodiode. An alternative to the embodiment shown in FIG. 4 may be fabricated if the beam size is large compared to the detector areas by placing detectors 580 and 640 in close proximity to each other and to eliminate beam splitter 630, thereby effecting a cost savings. Note, as above, the different equation that must be used for $f_B$ when reference mirror 560 is a retroreflector.

Figure 5:
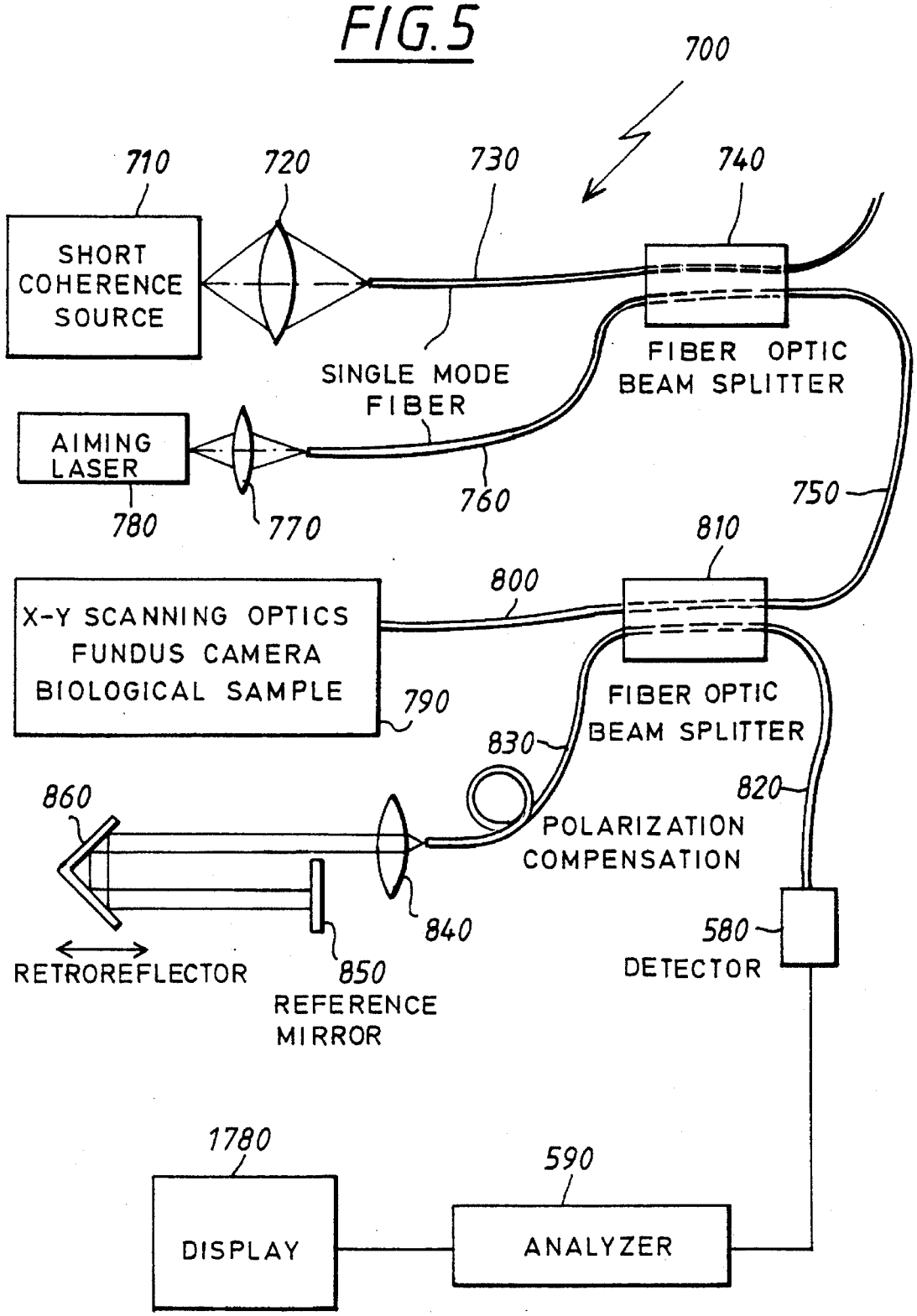
FIG. 5 shows, in pictorial form, an embodiment of the present invention which comprises a fiber optic based system which includes polarization compensating loop(s)

FIG. 5 shows, in pictorial form, embodiment 700 of the present invention which comprises a fiber optic based system which includes polarization compensating loop(s). As shown in FIG. 5, aiming laser 780 provides a visible output which is focused into the eye along with a sample beam. As is well known, the aiming laser enables an operator to determine the placement of the short coherence length sample beam. The aiming beam and the short coherent radiation are combined and coupled into fiber 750 by fiber optic beam splitter 740. Output from fiber 750 is split into a sample beam which enters fiber 800 and a reference beam which enters loop 830 by fiber optic beam splitter 810. The sample beam and aiming beam output by fiber 800 are directed to the patient's eye by x-y scanning optics 790 which is described in detail below in conjunction with FIG. 6. The reference beam output from fiber optic beam splitter 810 is coupled into polarization compensation loop 830. Polarization compensation loop 830 may comprise one or more loops. As is well known in the art, these loops function by adding a stress-induced birefringence into the fiber. The stress is caused by wrapping the fiber around a spool of predetermined size. Depending on the properties of the specific fiber used, and the availability of spool sizes, more than one such loop may be required to achieve the necessary compensation. In accordance with the present invention, compensating birefringence may be added by use of specifically oriented bends in the fiber or by using free beam wave plates external to the fiber or a combination thereof. The need for polarization compensation has been discovered in practice as the fibers tend to change the polarization of radiation in the sample arm relative to radiation in the reference arm and this acts to reduce the measured interference signal. In accordance with the present invention, retroreflector 860 is moved in fixed increments to provide spatial localization, for example, in the z-direction and frequency shifting is accomplished using one or more of the following methods. In accordance with the first method,, retroreflector 860 is scanned to provide a Doppler frequency of 4 V/λ. The Doppler frequency for the retroreflector provides a Doppler frequency of 4 V/λ because scanning the retroreflector at velocity V causes the optical path length to change at rate 4 V (The apparatus for scanning retroreflector 860 and for monitoring the speed of retroreflector 860 is not shown for clarity). In accordance with the second method, which may be used alone or in conjunction with the first method, acousto-optic modulators (which are well known) and/or piezo-electric transducers (which are well known) are attached to reference arm fiber 830. Then, in accordance with this second method, the length of reference arm fiber 830 is varied to provide the same type of optical path change that is provided by a moving reflector. Fiber optic beam splitters 740 and 810 are standard fiber optic beam splitters and such beam splitters are utilized in the telecommunications industry. Note that the methods and apparatus described above for obtaining velocity information in conjunction with the embodiments shown in FIGS. 3 and 4 are also applicable to the embodiment shown in FIG. 5.

Figure 6:
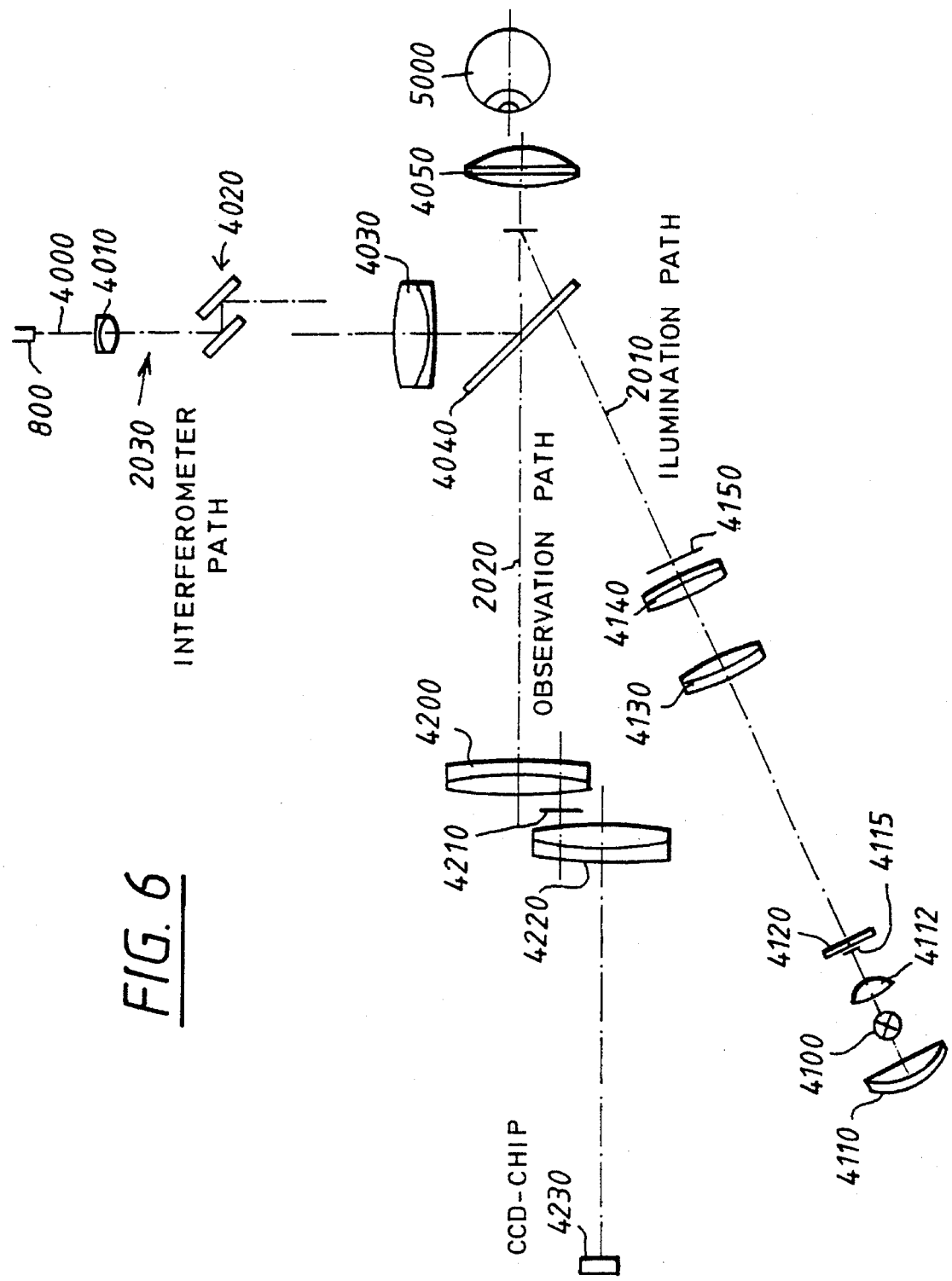
FIG. 6 shows, a block diagram of the x-y scanning optics of the apparatus shown in FIG. 5.

FIG. 6 shows, a block diagram of x-y scanning optics 790 of embodiment 700 shown in FIG. 5. As shown in FIG. 6, x-y scanning optics 790 is comprised of interferometer path 2030, illumination path 2010, and observation path 2020. Sample beam 4000 is output from fiber 800 is collimated by collimating lens 4010 and directed to x and y scanning mirrors 4020 which are driven by closed-loop galvanometers (not shown). The beam output from scanning mirrors 4020 is directed by scanning lens 4030 to beam splitter 4040. Lastly, beam splitter 4040 directs the sample beam to eye 5000 through ocular lens 4050. Ocular lens 4050 has, for example, aspherical faces and is user adjustable in the z-axis.

As shown in FIG. 6, illumination path 2010 comprises light source 4100, light source reflector 4110 (for example, a spherical reflector), condenser lens 4112, illumination slit aperture 4115, and fixation target 4120. Fixation target 4120 is user adjustable via motorized movement in the x and y axis to the extent of illumination slit aperture 4115. Slit collimating lens 4130 and slit imaging lens 4140 direct the illumination radiation through illumination pupil aperture 4150, beam splitter 4040 and to eye 5000 through ocular lens 4050.

As shown in FIG. 6, observation path 2020 comprises objective lens 4200, system aperture 4210 (not focused), CCD camera lens 4220, and CCD chip 4230.

Figure 7A:
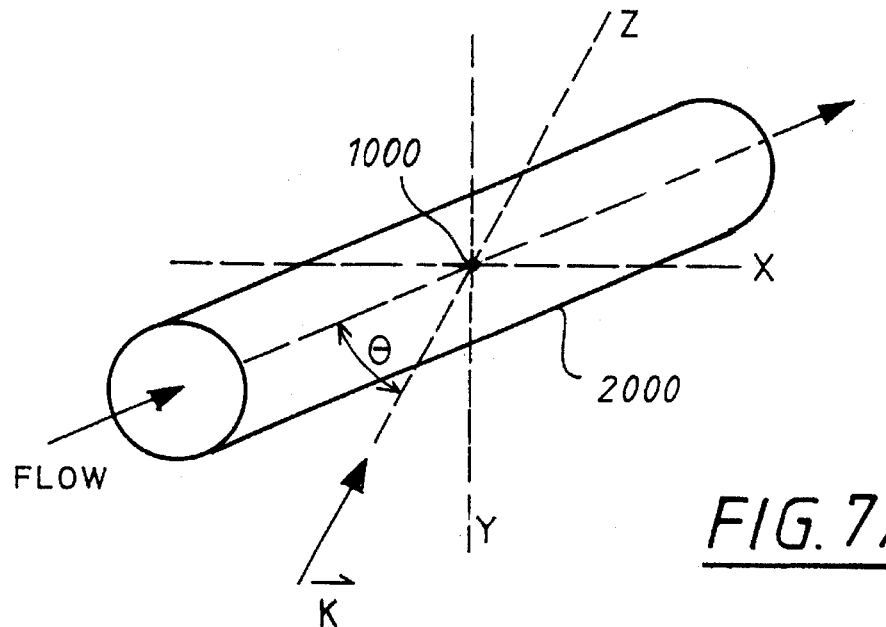
FIGS. 7A, 7B, and 7C illustrate, in pictorial form, the inventive method of determining absolute velocities using short coherence length interferometry.
Figure 7B:
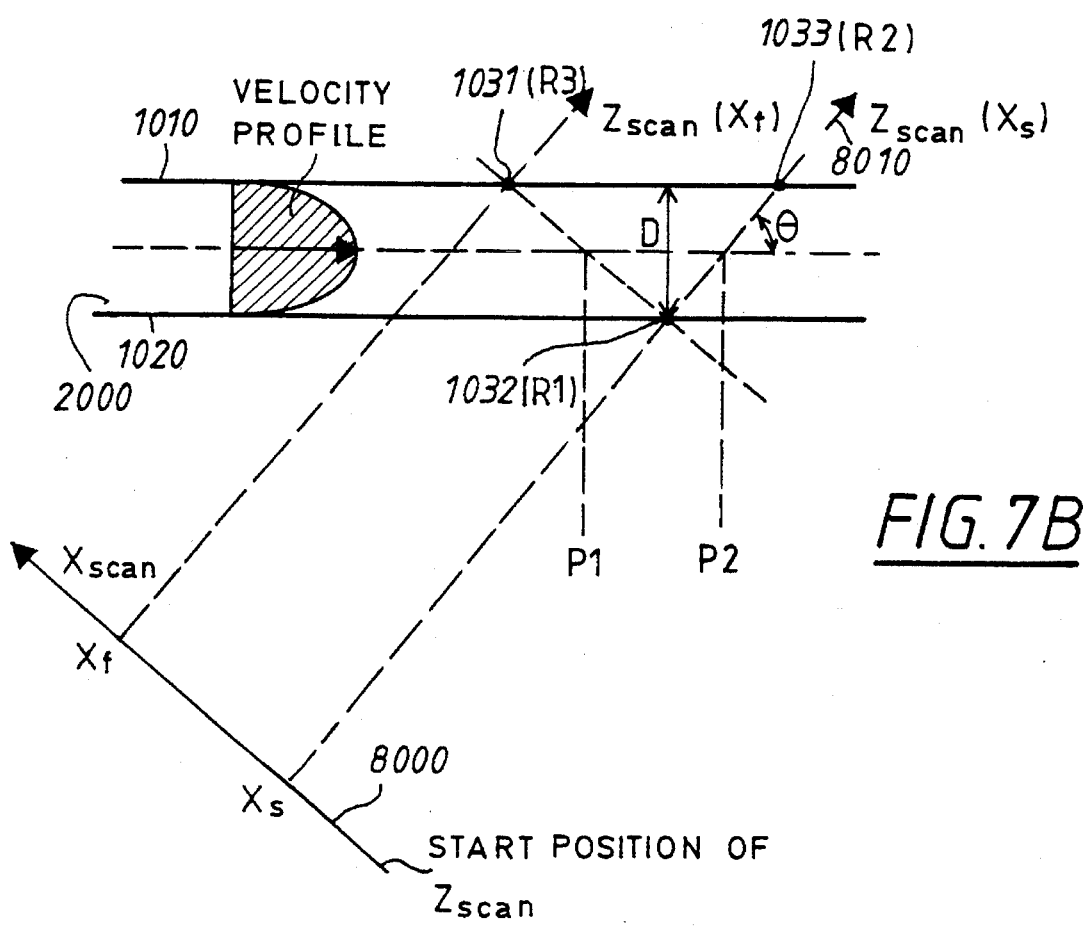
Figure 7C:
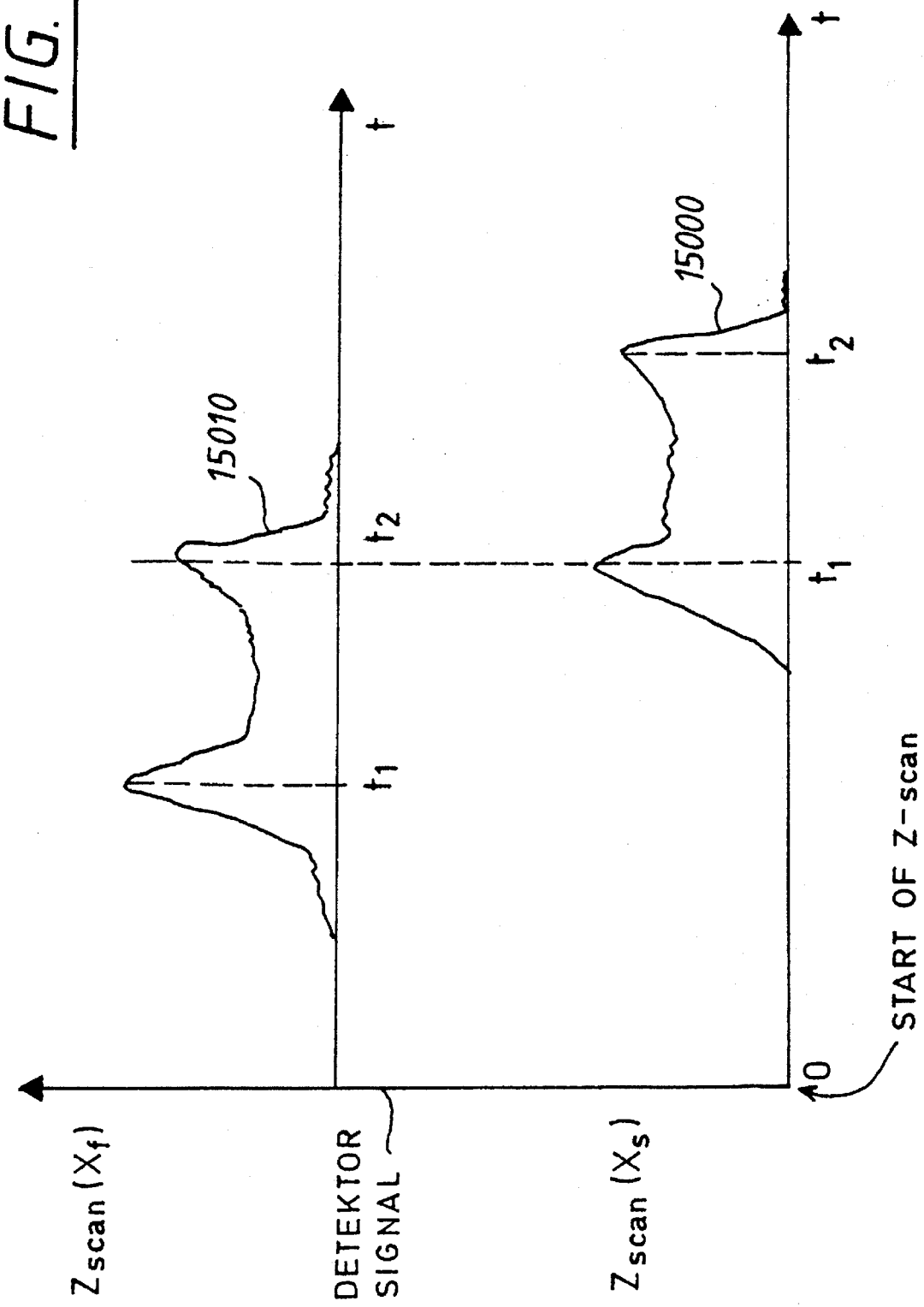

FIGS. 7A and 7B illustrate, in pictorial form, the inventive method of determining absolute velocities using short coherence length interferometry. In the choroid of an eye, i.e., the rear surface, there are a large number of easily seen blood vessels. In many instances, these blood vessels will be in a plane which is perpendicular to the direction of the incident light and therefore blood flowing therethrough will impart no Doppler shift. However, certain blood vessels, or portions thereof, of necessity, will be aligned into/out of the perpendicular plane and, therefore, blood flowing therein will have a parallel velocity component ($v_{\parallel}$) that will impart a measurable Doppler shift. The inventive method for obtaining the absolute blood flow velocity is described as follows in conjunction with FIGS. 7A, 7B, and 7C. Note that this description is taken in conjunction the embodiment 700 shown in FIGS. 5 and 6 for reference but is not limited by this choice.

(1) Locate blood vessel 2000 (see FIG. 7A). This is done visually, for example, using the fundus viewing optics of x-y scanning optics 790 shown in FIG. 6. Then, use x-y scanning optics 790 to place the aiming beam shown in FIG. 5 on the approximate midpoint of a blood vessel wall, shown as point 1000 in FIG. 7A. As one can readily appreciate, this also places the sample beam on point 1000.

(2) Locate the from and rear walls of the blood vessel by observing the strength of the interference signal output from detector 580. The strength is observed by a display of the output from detector 580 on display 1780 shown in FIG. 5 (An example of the output is given in FIG. 8B). In accordance with the present invention, and as shown in FIG. 7B, blood vessel walls 1010 and 1020 will produce a strong interference signal with zero Doppler shift at points 1031, 1032, and 1033. For the set-up shown in FIG. 7B, x-y scanning optics 790 is oriented so that the Y axis is perpendicular to blood vessel 2000. As a result, only scans in the X and Z directions are required. In this set-up, reflection/interference signals from points 1032 and 1033 are obtained by scanning in the Z direction.

As shown in FIG. 7B, line 8000 represents the start of a Z scan, which Z scan takes place along the direction indicated by arrow 8010. In accordance with a preferred embodiment of the present invention, the total length of the Z scan is fixed at, for example, approximately 1 mm and the optical depth of field of the interferometer path shown in FIG. 6 is designed to be at least 1 mm so that the light beam is always focused during a Z scan. The Z scan which goes through points R1 and R2 starts from line 8000 and has an X coordinate equal to $x_s$. The signal output from detector 580 during this Z scan is shown as signal 15000 in FIG. 7C. The peaks of signal 15000 correspond to points R1 and R2, respectively.

X scans are performed by stepping an X-mirror controller which comprises x and y scanning mirrors 4020 shown in FIG. 6. In the preferred embodiment of the present invention, x and y scanning mirrors 4020 are controlled directly by stepper motors which are controlled, in turn, by microprocessor 1740 of analyzer 590. In accordance with the present invention an X scan is accomplished as follows. Point R1 is located by an operator and a Z scan is made at X coordinate $x_s$ under processor control. The output from detector 580 is signal 15000 shown in FIG. 7C and the peaks are identified by peak detector 1730 of analyzer 590. In response to the signals from peak detector 1730, microprocessor 1740 of analyzer 590 measures and stores times $t_1$ and $t_2$ which are measured relative to the start of a Z scan. This information is used to determine $R2_z - R1_z$ from $R2_z - R1_z = (t_1 - t_2)^* v_r$. Next, incremental steps are taken by the x-scan mirror of x and y scanning mirrors 4020, typically 10 micron steps are taken. At each step along X, a Z scan is taken, in practice several Z scans are taken and the results are averaged for each increment in X. Times $t_1$ and $t_2$ are measured for each increment along X. For the set-up and geometry shown in FIG. 7B, as increments are taken along X, times $t_1$ and $t_2$ shift closer to the origin or time origin obtained from the first Z scan indicated by signal 15000 in FIG. 7C. At some point, $x_f$, time $t_2$ of the Z scan (see signal 15010 in FIG. 7C) coincides with time $t_1$ of the Z scan at $x_s$ (see signal 15000 in FIG. 7C). At this point $x_f - x_s = R3_x - R1_x$. These data are then used in the manner described below. Although the scan procedure is preferably implemented so that the scans are performed under processor control, those of ordinary skill in the art recognize that they can also be done manually.

(3) The unknown angle θ(the "out-of plane" angle) and the blood vessel diameter D are determined as follows:

$$\theta = \tan^{-1}\left[\frac{R3_x - R1_x}{R2_z - R1_z}\right] \quad (1)$$

and $$D = (R2_z - R1_z)\sin\theta = (R3_x - R1_x)\cos\theta \quad (2)$$

where R1 corresponds to point 1032 shown in FIG. 7B, R2 corresponds to point 1033 shown in FIG. 7B, R3 corresponds to point 103 1 shown in FIG. 7B, and the subscripts indicate the X and Z positions respectively.

Figure 1A:
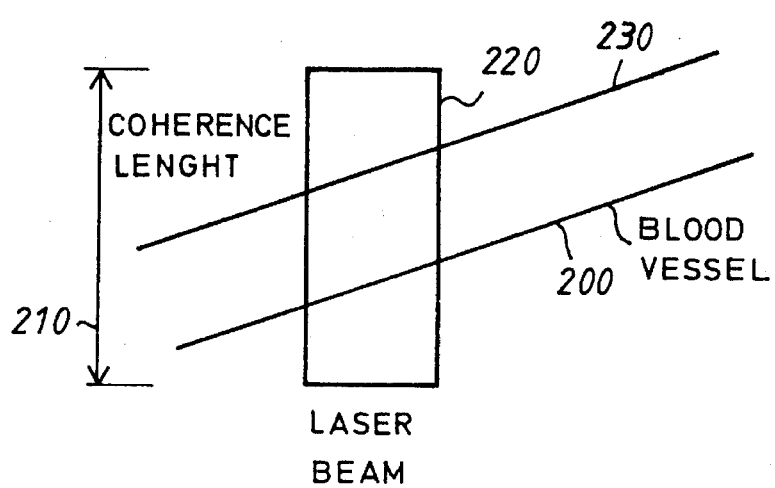
FIGS. 1A, 1B, and 1C provide an aid in understanding the drawbacks of the prior art long coherence length, Laser Doppler Velocimetry ("LDV")
Figure 1B:
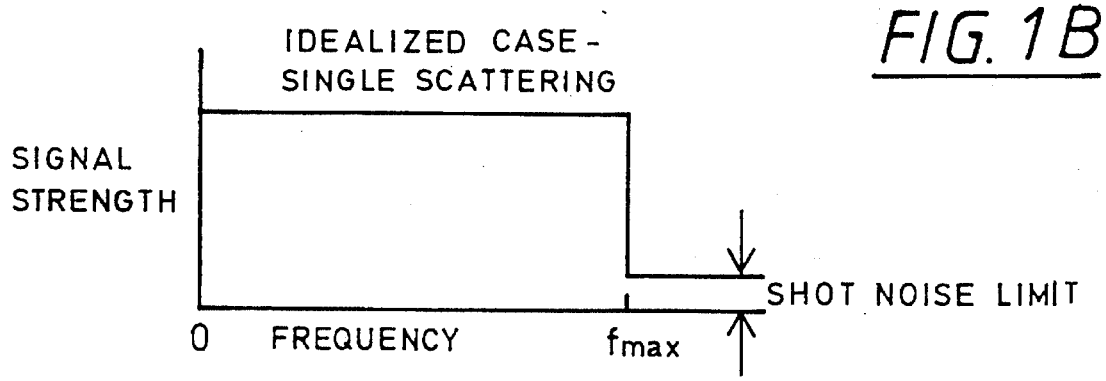
Figure 1C:
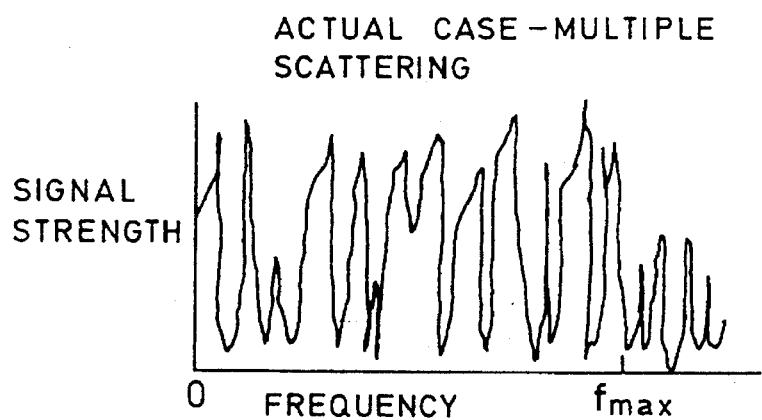

(4) As the Z and X scans are made, the Doppler shift frequency will grow, reach a peak, and decline to zero again (Note, in the example shown, the frequency shifts along X are positive and those along Z are negative—but we are concerned only with the absolute shifts). This is due to the parabolic velocity profile found in blood vessels which is given by:

$$V(r) = V_{max}\left(1 - \frac{r^2}{(D/2)^2}\right) \quad (3)$$

where r is the radial position measured from the longitudinal axis through the center of blood vessel 2000. A consequence of this parabolic velocity distribution (Poiseuille's Law) is that equal increments in Doppler shift frequency correspond to equal area concentric rings within the vessel, and each ring contributes equal signal strength (which accounts for the flat spectra of FIG. 1B in the case of long coherence length sources).

Therefore, knowing the angle θ and $v_\parallel$ at a particular value of z, it is straightforward to obtain the corresponding value of r and the absolute velocity at that corresponding value of r:

$$V_{abs} = v_\parallel / \cos\theta \quad (4)$$

(5) Due to scattering effects within the vessel, it may not always be possible to accurately determine point R2 (point 1033 in FIG. 7B) and point R3 (point 1031 in FIG. 7B). In this case, another method can be used to determine the absolute velocities. In accordance with this method, determine the location of the largest frequency shift during a scan along X and Z, these locations correspond to points P1 and P2 in FIG. 7B, respectively. Then:

$$\theta = \tan^{-1}\left(\frac{P1_x - R1_x}{P2_z - R1_z}\right) \quad (5)$$

and $$\frac{D}{2} = (P1_x - R1_x)\cos\theta = (P2_z - R1_z)\sin\theta \quad (6)$$

The difference values for points P1 and P2 used in eqn. (5) and (6) are obtained in a manner which is analogous to the timing method described above with respect to points R1, R2, and R3, except that here one looks for the peaks of frequency shift during the Z-scans instead of peaks in the interference signal. Typically, the procedure is initiated by an operator locating the desired blood vessel and the midpoint location on the blood vessel wall. The operator then orients the X-scan to lie in the plane of the blood vessel. Then, the computer causes the Z-scan and X-scan to take place in the manner described above to seek the peaks in the frequency shin (X and Y scans are delineated by cross hairs in the viewing optics). Once θ and D are known, the absolute velocities as a function of r can be determined as before.

If absolute blood speed values are not required, the above-described measurement of $v_\parallel$ is sufficient. For example, it will be quite valuable to monitor the advance/ remission of retinal vascular disease by comparing several values of $v_\parallel$ taken over time at the same location.

Although various modifications may be suggested by those versed in the art, it should be understood that we wish to embody within the scope of the patent granted hereon all such modification as reasonably and properly come within the scope of our contribution to the art.

Appendix A

Figure 10:
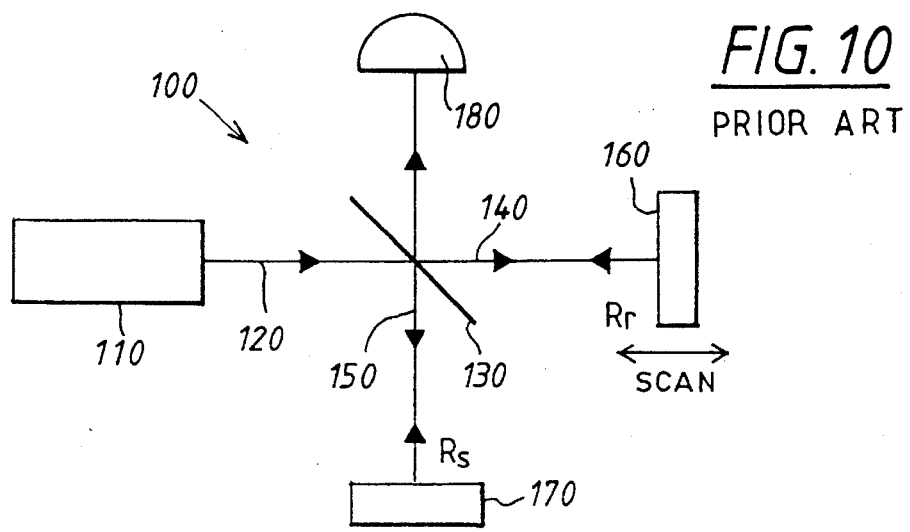
FIG. 10 shows, in pictorial form, a classical Michelson interferometer.

FIG. 10 shows, in pictorial form, a classical Michelson interferometer 100. As shown in FIG. 10, source light beam 120 emitted from source 110 is split at beam splitter 130 into two equal intensity beams, reference beam 140 and sample beam 150. Reference beam 140 is directed towards reference mirror 160 and sample beam 150 is directed towards sample mirror 170 (in measurement apparatus fabricated in accordance with the present invention, the retina becomes the sample mirror). Return light beams are directed back to beam splitter 130 by reference mirror 160 and sample mirror 170. At beam splitter 130 the two return beams converge and interfere. Beam splitter 130 causes the returned beams to be directed partially towards detector 180 and partially towards source 110. The relative amounts of each portion depends on the nature of the interference at that moment, i.e., constructive/destructive interference. The general theory of Doppler-shifted light and Michelson interferometry are well-known and can be found in many basic textbooks on physics and optics. Hence, only those aspects will be described which are needed for understanding the present invention. In accordance with the present invention, emphasis will be placed on combining short coherence length sources with Doppler velocimetry and extracting velocity information from a reflected beam.

For a monochromatic plane-wave source, the basic equation describing a measured signal seen at detector 180 of FIG. 10 is given by:

$$P_{det} = \frac{1}{4} I_o A (R_s + R_r) + \frac{1}{2}\sqrt{R_s R_r}\, I_o A \cos(2k\Delta l) \quad (A1)$$

where: $P_{det}$ is the measured power at detector 180; $I_o$ is the intensity of source light beam 120; $R_r$ is the reflectivity of reference mirror 160 (~1.0); $R_s$ is the reflectivity of the sample (unknown); k is the wave-vector of the light (=2 π/λ, where λ is the wavelength); Δl is the optical path length difference between the sample arm and the reference arm; and A is the area of detector 180.

The cosine term in eqn. (A1) describes the interference of the two beams, which in the case of pure monochromatic light (by definition pure monochromatic light has infinite coherence length) is simply periodic with Δl (the other terms are constant and are not useful here). If we relax the assumption of monochromatic light and introduce a broad band light source which has an intensity peak at a center frequency $f_o$ and which varies in intensity as a standard Gaussian function with width $\Delta f_o$; we can describe the intensity of this source using wave numbers, k (=2 π/λ=2 πf/c), as:

$$I(k) = I_o \exp\left[-\left(\frac{k_o}{\Delta k}\right)^2\right] \quad (A2)$$

where Δk is the width of the Gaussian light envelope function and $k_o$ is the center wave number.

The measured signal at detector 180 now becomes (accounting for all frequencies present in the source):

$$P_{det} = \frac{1}{2} \sqrt{R_s R_r} \exp\left[-\left(\frac{\Delta l}{l_c}\right)^2\right] \cos(2\Delta l k_o) \quad (A3)$$

where $l_c$ is called the coherence length and is defined as $2/\Delta k$. It can be seen that for path length mismatches much larger than $l_c$, the signal strength rapidly diminishes. Another viewpoint of this description is that a low coherence source emits short packets of coherent light, and if the return packets miss each other in time at the beam splitter due to path length differences, the interference signal will disappear. This short coherence length therefore allows one to determine the position of the sample mirror (if the reference mirror location is known) to within accuracy $l_c$. This is the basis of short coherence length interferometry for imaging purposes.

In practice, the instrument exhibits noise which interferes with the measurements. In general the noise arises from both the instrument and the inherent nature of the measurement. For example the instrument will exhibit Johnson noise (also known as white or thermal noise) which arises mainly in the resistive elements of the electronics; shot noise which is due to both the finiteness of the electron charge and the particulate nature of the blood flow, and 1/f noise (also known as pink noise) which has the characteristic that it has equal power per decade of frequency. The exact origins of 1/f noise are not well understood but it appears in both the instrument electronics (base current noise in transistors for example) and in the blood flow itself. The 1/f noise is the dominant noise in the velocimetry system; therefore low frequency Doppler shifts (such as those measured in previous LDV systems) will exhibit a high noise content. However, if the Doppler information can be carried on a frequency high enough that the 1/f noise is insignificant, low-noise measurements can be made.

One technique to carry the signal on a high modulation frequency is to scan the reference mirror at a known velocity, $v_r$. In this technique, eqn. (A3) becomes:

$$P_{det} = \frac{1}{2} \sqrt{R_s R_r} \, I_o A \exp\left[-\left(\frac{2v_r t}{l_c}\right)^2\right] \cos(2k_o v_r t) \quad (A4)$$

The Fourier transform of the above equation yields the frequency dependence of our signal:

$$P_{det} = \frac{\sqrt{\pi}}{4v_r} \sqrt{R_s R_r} \, I_o A l_c \exp\left[-\left(\frac{\pi l_c \{f - f_r\}}{2v_r}\right)^2\right] \quad (A5)$$

It can be seen from eqn. (A5) that the frequency content is peaked at $f_r$ where $f_r$ is the Doppler shift frequency ($=2v_r/\lambda$) and decreases as a Gaussian with width $l_c/2v_r$.

Finally, we now assume that the sample mirror is actually a red blood cell (RBC) that is moving at velocity $v_{RBC}$. Light reflected from the RBC will be Doppler shifted by an amount given by:

$$\Delta f_{RBC} = \frac{1}{2} \pi (K_i - K_s) \cdot v_{RBC} \quad (A6)$$

where $K_i$ is the k-vector of the incident light, $K_s$ is the k-vector of the scattered (reflected light), and $v_{RBC}$ is the velocity of the RBC. Note that all three quantities are vectors, i.e., they are direction dependent. Eqn. (A6) reduces to the simple scanning mirror Doppler shift if: (a) $v_{RBC}$ is small compared to the speed of light (as it is) so that $|K_i| \approx |K_s|$; (b) the direction of $v_{RBC}$ is parallel to $K_i$; and (c) $K_s$ is opposite in direction (i.e. reflected) to the incident light.

If we define $v_\parallel$ as the component of the RBC velocity which is parallel to the light direction, we can re-write eqn. (A5) as:

$$P_{det} = \frac{\sqrt{\pi}}{4v'} \sqrt{R_s R_r} \, I_o A l_c \exp\left[-\left(\frac{\pi l_c \{f - f'\}}{2v'}\right)^2\right] \quad (A7)$$

where $v'$ is $v' = v_r \pm v_\parallel$ and $f'$ is $2v'/\lambda$. Hence we see that the moving sample mirror has changed both the width (the Gaussian width is $l_c/v'$) and the center frequency of the signal. Therefore, by Fourier transforming the measured time-based signal, one can extract the parallel velocity component of the blood cell directly. That is, one performs a spectral analysis to determine the center frequency $f'$. In accordance with a preferred embodiment of the present invention, this is done by digitizing the signal and performing a fast Fourier transform in a manner which is well known to those of ordinary skill in the art.

What is claimed is:

1. Apparatus for measuring a profile of speed of blood, wherein the speed is parallel or antiparallel to the direction of a sample beam, the profile being across a blood vessel in a biological sample, in particular, in a retinal blood vessel, which apparatus comprises:

a source of a beam of radiation having a principal wavelength, which beam of radiation is substantially spatially coherent and has a temporal coherence length which is less than 1 picosecond;

means for splitting the beam into the sample beam and a reference beam;

means for reflecting the reference beam;

means for altering an optical path length of the reference beam from the splitting means to a detector means at an alteration velocity;

means for directing the sample beam within the biological sample to pass through the blood vessel;

wherein the detector means comprises means: (a) for detecting interferences between reflections of the sample beam from matter in the sample including matter situated across the blood vessel and reflections of the reference beam from the reflecting means and (b) for generating an interference signal;

analyzer means for analyzing the interference signal to determine the profile of the speed of the blood from an analysis of frequency spectra of time segments of the interference signal, the alteration velocity in the time segments, and the principal wavelength.

2. The apparatus of claim 1 wherein the analyzer means comprises means for determining, within a time segment, the speed of blood in a portion of the blood vessel from a central frequency of a frequency spectrum of the interference signal in the time segment, the alteration velocity in the time segment, and the principal wavelength.

3. The apparatus of claim 2 wherein the analyzer means further comprises means for determining, within the time segment, the speed of blood in the portion of the blood vessel from a width of the frequency spectrum of the interference signal in the time segment, the alteration velocity, the principal wavelength, and the temporal coherence length.

4. The apparatus of claim 3 wherein the analyzer means further comprises means for identifying the time segment which includes means for detecting maxima of an envelope of the interference signal.

5. The apparatus of claim 4 wherein the means for determining further comprises means for determining the profile of speed of blood from the interference signal generated during a single pass of the sample beam through the blood vessel.

6. The apparatus of claim 4 wherein means for determining further comprises means for determining the profile of speed of blood from interference signals generated during a multiplicity of passes of the sample beam through the blood vessel.

7. The apparatus of claim 1 wherein the source of the beam of radiation is a superluminescent light emitting diode, wherein the beam of radiation is focused through a pinhole aperture.

8. The apparatus of claim 1 wherein the source of the beam of radiation is a superluminescent light emitting diode, wherein the beam of radiation is coupled into a single mode optical fiber.

9. The apparatus of claim 1 wherein the means for reflecting the reference beam comprises at least one reflective surface and the means for altering comprises means for translating the means for reflecting.

10. The apparatus of claim 9 which further comprises means for determining the alteration velocity and for applying the alteration velocity as input to the analyzer means.

11. The apparatus of claim 10 wherein the means for translating outputs a position signal to the means for determining and the means for determining comprises means for differentiating the position signal to determine the alteration velocity.

12. The apparatus of claim 1 wherein the beam is coupled into an optical fiber and at least one portion of a path of travel within the apparatus of the sample beam and the reflections of the sample beam is comprised of an optical fiber and at least one portion of a path of travel within the apparatus of the reference beam is comprised of an optical fiber.

13. The apparatus of claim 12 wherein the means for reflecting comprises means for movement in fixed increments and the means for altering comprises one or more acousto-optic modulators attached to the optical fiber in the path of travel of the reference beam.

14. The apparatus of claim 13 wherein the means for altering further comprises means for translating the means for reflecting.

15. The apparatus of claim 12 wherein the means for reflecting comprises means for movement in fixed increments and the means for altering comprises one or more piezo-electric transducers attached to the optical fiber in the path of travel of the reference beam.

16. The apparatus of claim 15 wherein the means for altering further comprises means for translating the means for reflecting.

17. The apparatus of claim 1 wherein the length of the time segments is proportional to the temporal coherence length divided by the alteration velocity.

18. Method for measuring a profile of absolute value of velocity of blood across a blood vessel in a biological sample, in particular, in a retinal blood vessel, which method comprises the steps of:

generating a sample beam having a principal wavelength from a short coherence length Michelson interferometer having a reference beam whose reference beam path is varied at an alteration velocity;

aiming the sample beam at a wall of the blood vessel;

scanning the sample beam over the blood vessel in a first direction by varying the reference beam path at the alteration velocity and detecting an interference signal produced by an interference between reflections of the sample beam and the reference beam;

determining a first position of a first wall and a first position of a second wall from the interference signal;

determining components of velocity of the blood parallel or antiparallel to a direction of the sample beam from the interference signal by analyzing frequency spectra of time segments of the interference signal;

scanning the sample beam in a second direction to determine a second position of the second wall;

determining an angle of the first direction with respect to a direction of the blood vessel from the positions; and determining the absolute velocity profile of the blood from the components of velocity and the angle.

19. Method for measuring a profile of absolute value of velocity of blood across a blood vessel in a biological sample, in particular, in a retinal blood vessel, which method comprises the steps of:

generating a sample beam having a principal wavelength from a short coherence length Michelson interferometer having a reference beam whose reference beam path is varied at an alteration velocity;

aiming the sample beam at a wall of the blood vessel;

scanning the sample beam over the blood vessel in a first direction by varying the reference beam path at the alteration velocity and detecting an interference signal produced by an interference between reflections of the sample beam and the reference beam;

determining a first position of a first wall from the interference signal;

determining components of velocity of the blood parallel or antiparallel to a direction of the sample beam and a first position of a maximum of velocity from the interference signal by analyzing frequency spectra of time segments of the interference signal;

scanning the sample beam in a second direction to determine a second position of a maximum of velocity;

determining an angle of the first direction with respect to a direction of the blood vessel from the first position and the second position; and determining the absolute velocity profile of the blood from the components of velocity and the angle.

* * * * *